(12) United States Patent
Banerjee et al.

(10) Patent No.: US 10,377,684 B2
(45) Date of Patent: Aug. 13, 2019

(54) PROCESSES AND APPARATUSES FOR ISOMERIZING HYDROCARBONS

(71) Applicant: UOP LLC, Des Plaines, IL (US)

(72) Inventors: Soumendra Mohan Banerjee, New Delhi (IN); Steven C. Gimre, Carol Stream, IL (US)

(73) Assignee: UOP LLC, Des Plaines, IL (US)

( * ) Notice: Subject to any disclaimer, the term of this patent is extended or adjusted under 35 U.S.C. 154(b) by 11 days.

(21) Appl. No.: 15/783,214

(22) Filed: Oct. 13, 2017

(65) Prior Publication Data

US 2018/0037522 A1  Feb. 8, 2018

Related U.S. Application Data

(63) Continuation-in-part of application No. PCT/US2016/028073, filed on Apr. 18, 2016.

(51) Int. Cl.
*C07C 5/10* (2006.01)
*C07C 5/27* (2006.01)
(Continued)

(52) U.S. Cl.
CPC ............... *C07C 5/277* (2013.01); *C07C 5/10* (2013.01); *C10G 65/043* (2013.01); *C10G 65/08* (2013.01);
(Continued)

(58) Field of Classification Search
None
See application file for complete search history.

(56) References Cited

U.S. PATENT DOCUMENTS 2,394,694 A   2/1946  Kanhofer
2,399,765 A   5/1946  Shoemaker
(Continued)

FOREIGN PATENT DOCUMENTS

EP   0256604 B1   6/1991
EP   1243332 A1   9/2002
(Continued)

OTHER PUBLICATIONS

Yildirim et al. ("Dividing wall columns in chemical process industry: A review on current activities", Separation and Purification Technology 80, 403-417). (Year: 2011).*
(Continued)

*Primary Examiner* — In Suk C Bullock
*Assistant Examiner* — Ali Z Fadhel

(57) ABSTRACT

Processes and apparatuses for isomerizing hydrocarbons are provided. In an embodiment, a process for isomerizing hydrocarbons includes providing a first hydrocarbon feed that includes hydrocarbons having from 5 to 7 carbon atoms. The first hydrocarbon feed is fractionated to produce a first separated stream that includes hydrocarbons having from 5 to 6 carbon atoms and a second separated stream that includes hydrocarbons having 7 carbon atoms. The first separated stream is contacted with a benzene saturation catalyst at benzene saturation conditions to produce an intermediate stream and subsequently isomerized in the presence of a first isomerization catalyst and hydrogen under first isomerization conditions to produce a first isomerized stream. The second separated stream is isomerized in the presence of a second isomerization catalyst and hydrogen under second isomerization conditions that are different from the first isomerization conditions to produce a second isomerized stream.

13 Claims, 1 Drawing Sheet

(51) Int. Cl.
*C07C 13/18* (2006.01)
*C10G 65/04* (2006.01)
*C10G 65/08* (2006.01)

(52) U.S. Cl.
CPC .... *C07C 2521/06* (2013.01); *C07C 2527/126* (2013.01); *C07C 2601/14* (2017.05)

(56) References Cited

U.S. PATENT DOCUMENTS

| | | | |
|---|---|---|---|
| 2,461,598 | A | 2/1949 | Gibson |
| 2,513,103 | A | 6/1950 | Passino |
| 2,530,875 | A | 11/1950 | Gwynn |
| 2,785,208 | A | 3/1957 | Bain et al. |
| 2,965,694 | A | 12/1960 | Stanley |
| 3,066,176 | A | 11/1962 | Schwarzenbek |
| 4,834,866 | A | 5/1989 | Schmidt |
| 5,235,120 | A * | 8/1993 | Bogdan ............... C10G 59/02 208/57 |
| 5,334,792 | A * | 8/1994 | Del Rossi ........... C10G 59/02 585/314 |
| 5,382,730 | A * | 1/1995 | Breckenridge ........ C07C 5/10 208/60 |
| 5,382,731 | A * | 1/1995 | Chang ................. C07C 5/13 585/310 |
| 5,705,731 | A | 1/1998 | Lin et al. |
| 5,830,345 | A * | 11/1998 | Lee ..................... C10G 45/54 208/92 |
| 6,338,791 | B1 * | 1/2002 | Ragil ................... C10G 45/58 208/133 |
| 7,429,685 | B2 | 9/2008 | Bouchy |
| 2004/0254415 | A1 * | 12/2004 | Bouchy ............... C10G 65/14 585/739 |
| 2006/0270885 | A1 * | 11/2006 | Boyer .................. C07C 5/2791 585/741 |
| 2007/0167663 | A1 * | 7/2007 | Boyer .................. C07C 5/2791 585/750 |
| 2008/0287724 | A1 * | 11/2008 | Shecterle ............... C07C 5/10 585/735 |
| 2015/0166438 | A1 | 6/2015 | Glover |

FOREIGN PATENT DOCUMENTS

| | | |
|---|---|---|
| RU | 2307820 C1 | 10/2007 |
| RU | 2540272 C2 | 2/2015 |
| WO | 2016176069 A1 | 11/2016 |

OTHER PUBLICATIONS

Yildirim, "Dividing wall columns in chemical process industry: A review on current activities", Separation and Purification Technology 80 (2011) 403-417.

Search Report dated Sep. 15, 2016 for corresponding PCT Appl. No. PCT/US2016/28073.

* cited by examiner

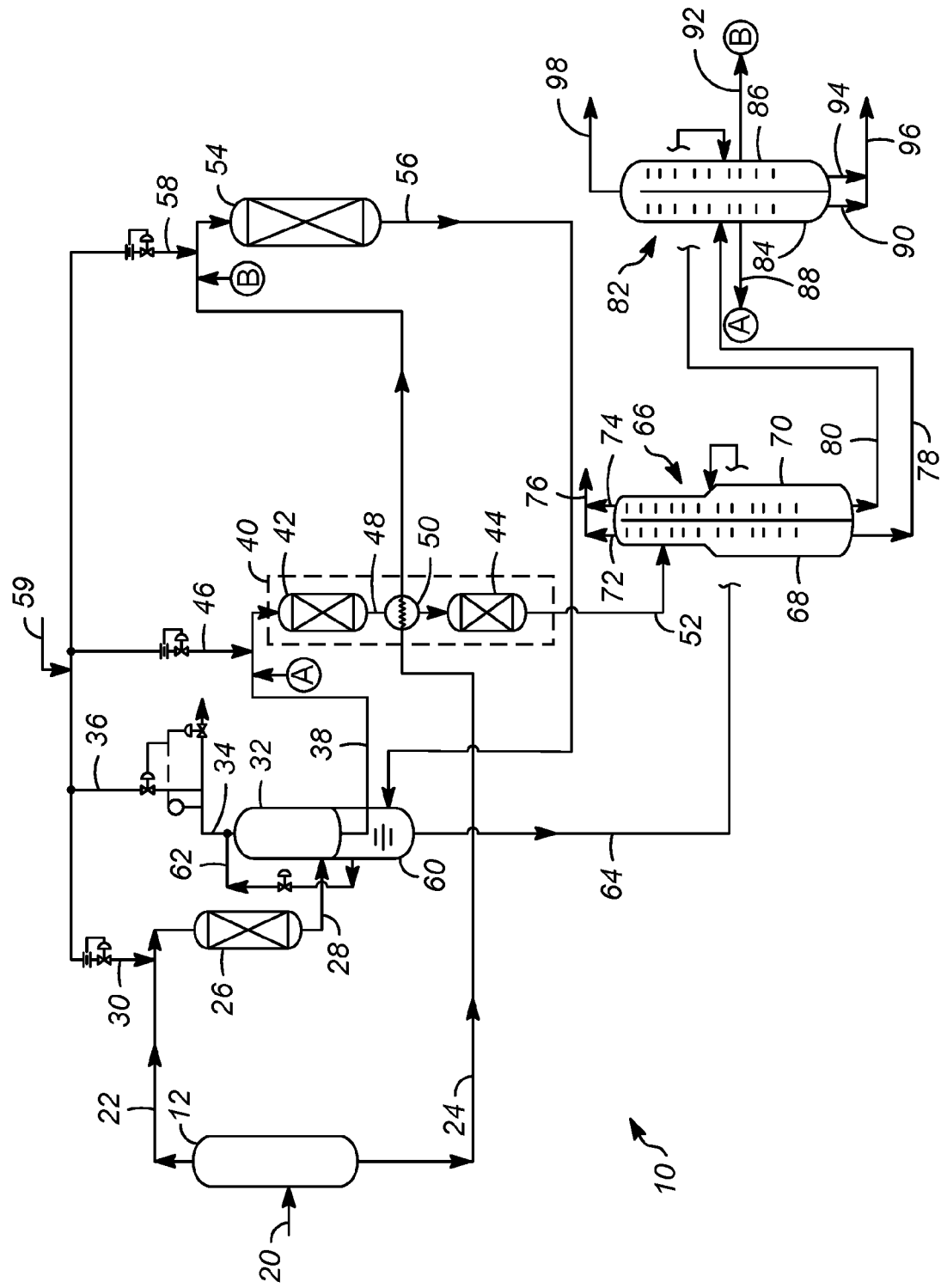

PROCESSES AND APPARATUSES FOR ISOMERIZING HYDROCARBONS

CROSS-REFERENCE TO RELATED APPLICATIONS

This application is a Continuation-In-Part of International Application No. PCT/US2016/028073 filed Apr. 18, 2016, which application claims priority from U.S. application Ser. No. 14/696,799 filed Apr. 27, 2015, now abandoned, the contents of which cited applications are hereby incorporated by reference in their entirety.

TECHNICAL FIELD

The technical field generally relates to processes and apparatuses for isomerizing hydrocarbons. More particularly, the technical field relates to processes and apparatuses for separately isomerizing a stream containing $C_5$ and $C_6$ hydrocarbons, and a stream containing $C_7$ hydrocarbons.

BACKGROUND

Hydrocarbon streams are refined through various unit operations to produce various types of fuel, industrial raw materials that are employed in production of other compounds or products, and petroleum-based products. Production of gasoline is a particularly important industrial process involving refining of hydrocarbons through various unit operations, including isomerization and catalytic reforming. Reforming of hydrocarbons is useful to convert paraffins to aromatic compounds in the presence of noble metal catalysts. Aromatic compounds provide high octane value and, thus, are desirable components in gasoline. Isomerization is effective to convert linear hydrocarbons into branched hydrocarbons, which have a higher octane value than linear compounds but a lower octane value than aromatic compounds. Isomerized streams (or isomerate) is substantially free of aromatic compounds, whereas reformate streams (or reformate) generally include high quantities of aromatic compounds (e.g., at least 50 wt %).

During refining, a hydrocarbon stream is generally separated into various streams based on the number of carbon atoms of compounds within each stream. Hydrocarbons having 7 or more carbon atoms are generally subject to reforming because reforming generally results in higher octane value than isomerization of these hydrocarbons. Hydrocarbons having 5 or 6 carbon atoms are generally subjected to isomerization.

Modern specifications for gasoline typically place limits on aromatic content. The limits on aromatic content restrict the amount of reformate that can be blended into the gasoline. Since refineries generally produce significantly more hydrocarbons having 7 or more carbon atoms, there is typically too much reformate produced relative to isomerate for cases where aromatics are highly restricted in gasoline. Hydrocarbons having 7 carbon atoms cannot be effectively isomerized with hydrocarbons having 5 or 6 carbon atoms, since hydrocarbons having 7 carbon atoms are subjected to cracking under conditions necessary to effectively isomerize hydrocarbons having 5 or 6 carbon atoms.

Accordingly, it is desirable to provide apparatuses and processes for isomerizing hydrocarbons that enable hydrocarbons having 5 or 6 carbon atoms and hydrocarbons having 7 carbon atoms to be separately and effectively isomerized. Furthermore, other desirable features and characteristics of the present subject matter will become apparent from the subsequent detailed description of the subject matter and the appended claims, taken in conjunction with the accompanying drawings and this background of the subject matter.

BRIEF SUMMARY

Various embodiments contemplated herein relate to processes and apparatuses for isomerizing hydrocarbons. The exemplary embodiments taught herein separately isomerize hydrocarbons having 5 or 6 carbon atoms and hydrocarbons having 7 carbon atoms.

In an embodiment, a process for isomerizing hydrocarbons includes providing a first hydrocarbon feed comprising hydrocarbons having from 5 to 7 carbon atoms. The first hydrocarbon feed is fractionated to produce a first separated stream comprising hydrocarbons having from 5 to 6 carbon atoms and comprising benzene and a second separated stream comprising hydrocarbons having 7 carbon atoms. The first separated stream is contacted with a benzene saturation catalyst at benzene saturation conditions to produce an intermediate stream comprising cyclohexane. The intermediate stream is isomerized in the presence of a first isomerization catalyst and hydrogen under first isomerization conditions to produce a first isomerized stream. The second separated stream is isomerized in the presence of a second isomerization catalyst and hydrogen under second isomerization conditions to produce a second isomerized stream.

In another embodiment, a process for isomerizing hydrocarbons includes providing a first hydrocarbon feed comprising hydrocarbons having from 5 to 7 carbon atoms. The first hydrocarbon feed is fractionated to produce a first separated stream comprising hydrocarbons having from 5 to 6 carbon atoms and comprising benzene and a second separated stream comprising hydrocarbons having 7 carbon atoms. The first separated stream is contacted with a benzene saturation catalyst at benzene saturation conditions to produce an intermediate stream comprising cyclohexane. A first flash drum overhead stream comprising butane and lighter boiling hydrocarbons and gases is separated from the intermediate stream in a first flash drum to provide a net first flash drum bottoms stream. The net first flash drum bottoms stream is isomerized in the presence of a first isomerization catalyst and hydrogen under first isomerization conditions to produce a first isomerized stream. The second separated stream is isomerized in the presence of a second isomerization catalyst and hydrogen under second isomerization conditions to produce a second isomerized stream. A second flash drum overhead stream comprising butane and lighter boiling hydrocarbons and gases is separated from the second isomerized stream in a second flash drum to provide a second flash drum bottoms stream. The first isomerized stream and second flash drum bottoms stream are stabilized to provide a first isomerized stabilized stream and a second isomerized stabilized stream. The first isomerized stabilized stream and the second isomerized stabilized stream are passed to a split shell column comprising a deisohexanizer and a deisoheptanizer to provide a net isomerate product.

In yet another embodiment, an apparatus for isomerizing hydrocarbons includes a first fractionation unit adapted to fractionate a first hydrocarbon feed comprising hydrocarbons having from 5 to 7 carbon atoms to produce a first separated stream comprising hydrocarbons having from 5 to 6 carbon atoms and a second separated stream comprising hydrocarbons having 7 carbon atoms. A benzene saturation reactor in fluid communication with the first fractionation unit produces an intermediate stream comprising cyclohexane. A first isomerization unit in fluid communication with the benzene saturation reactor and adapted to receive and isomerize the intermediate stream in the presence of a first isomerization catalyst and hydrogen under first isomerization conditions produces a first isomerized stream. A second isomerization unit in fluid communication with the first fractionation unit is adapted to receive and isomerize the second separated stream in the presence of a second isomerization catalyst and hydrogen under second isomerization conditions to produce a second isomerization stream.

BRIEF DESCRIPTION OF THE DRAWINGS

The various embodiments will hereinafter be described in conjunction with the following drawing figures, wherein like numerals denote like elements, and wherein:

FIGURE is a schematic diagram of a process and an apparatus for isomerizing hydrocarbons in accordance with an exemplary embodiment.

DETAILED DESCRIPTION

The following detailed description is merely exemplary in nature and is not intended to limit the various embodiments or the application and uses thereof. Furthermore, there is no intention to be bound by any theory presented in the preceding background or the following detailed description.

Processes and apparatuses for isomerizing hydrocarbons are provided herein. The processes and apparatuses enable a first separated stream that includes hydrocarbons having 5 or 6 carbon atoms and a second separated stream that includes hydrocarbons having 7 carbon atoms to be separately and effectively isomerized. In particular, a first isomerization catalyst is employed for isomerization of the first separated stream to produce a first isomerized stream and a second isomerization catalyst is employed for isomerization of the second separated stream to produce a second isomerized stream. The first isomerization catalyst and the second isomerization catalysts may be different or may be the same type or family. The first isomerization catalyst and the second isomerization catalyst may be chlorided alumina in embodiments, or zirconia-containing catalyst in other embodiments. Chlorided alumina catalysts generally require drying of the stream to be isomerized. In this embodiment, a common dryer may be employed prior to isomerization of the respective separated streams. In another example, processes and apparatuses that employ zirconia-containing isomerization catalysts do not incorporate drying of the stream to be isomerized. The first separated stream and the second separated stream are subject to different isomerization conditions particular to the hydrocarbon species contained in the respective streams.

Prior to introduction to the first isomerization zone, the first separated stream is contacted with a benzene saturation catalyst at benzene saturation conditions to produce an intermediate stream comprising cyclohexane. The first separated stream may be subject to slower space velocity and/or higher temperatures than the second separated stream, thereby minimizing cracking of the hydrocarbons having 7 carbon atoms while still effectively isomerizing the hydrocarbons having 5 or 6 carbon atoms. The first isomerized stream and the second isomerized stream are stabilized in a split shell stabilizer. Intervening unit operations such as a liquid/vapor separation to first separate hydrogen and lighter gases may be present. Stabilization produces a light stream that includes hydrocarbons having less than or equal to 4 carbon atoms, a first isomerized stabilized stream, and the second isomerized stabilized stream that includes branched hydrocarbons. Subsequently, the first isomerized stabilized stream and the second isomerized stabilized stream are provided to a split shell column including a deisohexanizer and a deisoheptanizer. Additional unit operations may be consolidated as described in further detail below, thereby maximizing processing efficiency and minimizing costs while enabling effective isomerization of $C_5$, $C_6$, and $C_7$ hydrocarbons.

An embodiment of a process for isomerizing hydrocarbons is addressed with reference to an apparatus and process 10 for isomerizing hydrocarbons as shown in the FIGURE. In accordance with the process and as shown in the FIGURE, a first hydrocarbon feed 20 is provided. The first hydrocarbon feed 20 includes hydrocarbons that have from 5 to 7 carbon atoms, and may further include various other hydrocarbons including hydrocarbons having 8 or more carbon atoms. The hydrocarbons included in the first hydrocarbon feed 20 may be aromatic, aliphatic saturated, aliphatic unsaturated, or cyclic hydrocarbons. The first hydrocarbon feed 20 is generally depleted of hydrocarbons that have less than 5 carbon atoms since such hydrocarbons are generally employed in other industrial processes. The first hydrocarbon feed 20 may include fresh feed, recycled feed, or by-products from refining of other fractions derived from petroleum. In other embodiments, the first hydrocarbon feed 20 may be a fraction that contains at least 95 wt-% hydrocarbons only having from 5 to 7 carbon atoms.

In accordance with the processes described herein, the first hydrocarbon feed 20 is fractionated to produce a first separated stream 22 from an overhead of the fractionation unit 12 that includes hydrocarbons having from 5 to 6 carbon atoms and a second separated stream 24 from a bottoms of the fractionation unit 12 having hydrocarbons having 7 carbon atoms. Fractionation may be conducted through conventional distillation in a first fractionation unit 12, which may include one or more distillation columns that are adapted to fractionate the first hydrocarbon feed 20 to produce the first separated stream 22 and the second separated stream 24.

In embodiments, the first hydrocarbon feed 20 is fractionated to provide hydrocarbons having from 5 to 6 carbon atoms in the first separated stream 22 while substantially excluding hydrocarbons having more than 6 carbon atoms. By "substantially excluding", it is meant that the hydrocarbons having 7 carbon atoms may be present in amounts of less than about 5 wt. % based on the total weight of the first separated stream 22. In an embodiment, the first separated stream comprising hydrocarbons having from 5 to 6 carbon atoms has less than about 3 wt-% hydrocarbons having more than 6 carbon atoms. In another embodiment, the first separated stream comprising hydrocarbons having from 5 to 6 carbon atoms has less than about 1 wt-% hydrocarbons having more than 6 carbon atoms. The second separated stream 24 is taken as a bottoms stream to include aliphatic and aromatic hydrocarbons having 7 carbon atoms, and also generally includes hydrocarbons having 5 or 6 carbon atoms. In one example, hydrocarbons having 5 or 6 carbon atoms may be present in amounts less than about 0.5% based on the total weight of the second separated stream 24. In an exemplary embodiment, the TBP end point of the second separated stream 24 should be in the range from about 107° C. to about 110° C. and should not exceed 110° C.

The first separated stream 22 is passed through a benzene saturation reactor 26. The benzene saturation reactor 26 is designed to saturate benzene present in the first separated stream 22. The first separated stream 22 is contacted with a benzene saturation catalyst at benzene saturation conditions in the benzene saturation reactor 26 to produce an intermediate stream 28 comprising cyclohexane. The benzene saturation conditions includes a temperature from about 130° C. to about 160° C. and a pressure from about 15 Kg/cm$^2$ g to 25 Kg/cm$^2$ g, preferably from about 18 Kg/cm$^2$ g to about 22 Kg/cm$^2$ g. In various embodiments, hydrogen may be provided in desired amounts to an inlet of the benzene saturation reactor 26 through a line 30 via a valve as shown in the FIGURE. In one example, hydrogen is introduced as dry hydrogen after passing through one or more driers. The temperature rise across the benzene saturation reactor 26 depends on the amount of benzene present in the first separated stream 22. In accordance with an exemplary embodiment, the temperature rise is controlled in the range of about 3° C. to about 5° C. by recycling a portion of the intermediate stream 28 (not shown) to the inlet of the benzene saturation reactor 26 after cooling. Further, in an exemplary embodiment, the benzene saturation conditions include a outlet temperature of about 130° C. to about 150° C. and a outlet pressure of about 18 Kg/cm$^2$ g to about 20 Kg/cm$^2$ g. Examples of benzene saturation catalysts include platinum group, tin or cobalt and molybdenum metals on suitable refractory inorganic oxide supports such as alumina. In one embodiment, the alumina is an anhydrous gamma-alumina with a high degree of purity. The term platinum group metals refer to noble metals excluding silver and gold which are selected from the group consisting of platinum, palladium, germanium, ruthenium, rhodium, osmium, and iridium.

The intermediate stream 28 is passed to a first flash drum 32 to separate a first flash drum overhead stream 34 including butane and lighter boiling hydrocarbons and gases. In an exemplary embodiment, the pressure in the first flash drum 32 is maintained by a push pull system as shown in the FIGURE using hydrogen introduced via line 36 through a valve as shown. In one example, hydrogen is introduced as dry hydrogen after passing through one or more driers. A net first flash drum bottoms stream 38 is sent to a first isomerization unit 40. The first isomerization unit 40 may include one or more reactors and accordingly the isomerization may take place in stages.

In an exemplary embodiment as shown in the FIGURE, the isomerization unit 40 includes a first stage isomerization reactor 42 and a second stage isomerization reactor 44. A first stage of isomerization takes place in the first stage isomerization reactor 42. Following the first stage of isomerization, a first interstage isomerization effluent in line 48 is exchanged in a heat exchanger 50 against the second separated stream 24. Line 48 then carries the partially cooled first interstage isomerization effluent from the first stage isomerization reactor 42 to the second stage isomerization reactor 44. After further isomerization in the second stage isomerization reactor 44, a first isomerized stream 52 is produced.

After the heat exchange with the effluent in line 48, the second separated stream 24 is sent to a second isomerization unit 54 that is separate from the first isomerization unit 40. The second isomerization unit 54 is in fluid communication with the first fractionation unit 12 and is adapted to receive and isomerize the second separated stream 24. In one example, the second isomerization unit 54 may include of one or more reactors and isomerization may take place in stages. A second isomerized stream 56 is obtained from the second isomerization unit 54.

As illustrated in the FIGURE, the first separated stream 22, after passing through the benzene saturation reactor 26 and the first flash drum 32, is isomerized in the presence of a first isomerization catalyst and hydrogen under first isomerization conditions to produce the first isomerized stream 52, and the second separated stream 24 is isomerized in the presence of a second isomerization catalyst and hydrogen under second isomerization conditions that are different from the first isomerization conditions to produce the second isomerized stream 56. In an exemplary embodiment as shown in the FIGURE, hydrogen is provided to the inlet of the first isomerization unit 40 and the second isomerization unit 54 via line 46 and line 58, respectively, through respective valves as shown in the FIGURE. No hydrogen recycle may be required because substantially all of the hydrogen is consumed in the first isomerization unit 40 and the second isomerization unit 54. In one example, hydrogen is introduced as dry hydrogen after passing through one or more driers. In another example, static mixers are used at the inlet of the first isomerization unit 40 and the second isomerization unit 54 to ensure proper mixing of the hydrogen with the liquid phase.

The first isomerization catalyst and the second isomerization catalyst may be different or they may be the same type of isomerization catalyst. The first separated stream 22 and the second separated stream 24 are separately isomerized because hydrocarbons having 7 carbon atoms generally crack under conditions that are ideal for isomerizing hydrocarbons that have 5 or 6 carbon atoms. Isomerization of the second separated stream 24 is generally conducted at lower temperature and pressure defined below in the paragraph than the first separated stream 22, and the hydrocarbons having 5 or 6 carbon atoms are generally inert under the lower temperature and pressure at which the second separated stream 24 is isomerized. In embodiments, the second separated stream 24 is isomerized at a higher space velocity than a space velocity of the first separated stream 22. While particular space velocities at which the first separated stream 22 and the second separated stream 24 are isomerized may vary depending upon numerous variables including particular isomerization catalysts and isomerization units used, as well as isomerization temperature, typical space velocities range from about 0.5 to about 20. The first separated stream 22 may be isomerized at lower values within the aforementioned range, such as from about 0.5 to about 6, preferably from about 1 to about 4 and the second separated stream 24 may be isomerized at higher values within the aforementioned range, such as from about 2 to about 20, preferably from about 5 to about 8. The first separated stream is isomerized at lower space velocities than the second separated stream. In addition to or as an alternative to different space velocities, the second separated stream 24 may be isomerized at a lower isomerization temperature than an isomerization temperature of the first separated stream 22. Isomerization temperatures are also subject to the above-referenced variables, although typical isomerization temperatures range from about 60° C. to about 210° C. The first separated stream 22 may be isomerized at higher values within the aforementioned range, such as from about 130° C. to about 210° C. and a pressure of about 28 Kg/cm$^2$ g to about 34 Kg/cm$^2$ g, and the second separated stream 24 may be isomerized at lower values within the aforementioned range, such as from about 100° C. to about 120° C. and a pressure of about 20 Kg/cm$^2$ g to about 34 Kg/cm$^2$ g.

As set forth above, the first isomerization catalyst and the second isomerization catalyst may be different or they may be the same type of isomerization catalyst and may be either of one of a zirconia containing catalyst or a chlorided alumina catalyst. In an embodiment, chlorided alumina is employed as the first isomerization catalyst and the second isomerization catalyst. In another embodiment, chlorided alumina is employed as the first isomerization catalyst and zirconia containing catalyst is employed as the second isomerization catalyst. In yet another embodiment, zirconia containing catalyst is employed as the first isomerization catalyst and the chlorided alumina is employed as the second isomerization catalyst. In still another embodiment, zirconia containing catalyst is employed as the first isomerization catalyst and the second isomerization catalyst. Chlorided alumina catalysts generally require drying of the stream to be isomerized, in embodiments; a common dryer may be employed prior to isomerization of the respective separated streams. As another example, processes and apparatuses that employ zirconia-containing isomerization catalysts can tolerate higher levels of water, sulfur, nitrogen and do not incorporate drying of the stream to be isomerized. Also, zirconia-containing catalyst do not need any chloride injection. This eliminates the need of the caustic scrubber to treat the off gases before they can be routed to the refinery fuel gas pool.

The chlorided alumina may include, for example, chlorided platinum alumina catalyst. The alumina can be an anhydrous gamma-alumina, although other aluminas may be utilized. In addition to platinum, the isomerization catalysts may optionally include one or more of palladium, germanium, ruthenium, rhodium, osmium, and iridium. The isomerization catalysts may contain from about 0.1 to about 0.25 wt % platinum, and optionally from about 0.1 wt % to about 0.25 wt % of one or more of palladium, germanium, ruthenium, rhodium, osmium, and iridium, based on the total weight of the isomerization catalyst. Because chlorided alumina catalysts generally require drying of the stream to be isomerized, in an embodiment using chlorided alumina catalyst, the respective stream may be dried prior to the isomerization with the chlorided alumina catalyst, and drying may be conducted through conventional drying techniques. Suitable zirconia-containing catalysts include, for example, noble metal such as platinum on sulfated or tungstated zirconia. In one example, sulfated or tungstated zirconium dioxide in combination with aluminum oxide, manganese oxide, titanium oxide and iron oxide may be used. The hydrogenating component may include one of platinum, palladium, nickel, gallium or zinc. Unlike chlorided alumina, zirconia-containing catalysts are not as selective as chlorided alumina catalysts and may incorporate a hydrogen recycle to both the first isomerization unit 40 and the second isomerization unit 54.

After isomerization, the first isomerized stream 52 and the second isomerized stream 56 are sent to a split shell stabilizer 66. In an exemplary embodiment as shown in the FIGURE, the second isomerized stream 56 may be passed through a second flash drum 60 and subsequently the second flash drum bottoms stream 64 is sent to the split shell stabilizer 66. In an exemplary embodiment, the first flash drum 32 is stacked with the second flash drum 60. Preferably, the first flash drum 32 is stacked on the second flash drum 60 as shown in the FIGURE and the second flash drum overhead stream 62 combines with the first flash drum overhead stream 34.

As illustrated, the split shell stabilizer 66 includes a first side 68 and a second side 70. The first side 68 and the second side 70 are separated by a partition as shown in the FIGURE. In one embodiment, the partition my not extend up to the top of the split shell stabilizer 66. The first side 68 of the split shell stabilizer is configured to stabilize the first isomerized stream 52 and the second side 70 of split shell stabilizer is configured to stabilize the second isomerized stream 56 that remains in the second flash drum bottoms stream 64. Accordingly, the first isomerized stream 52 is sent to the first side 68 and the second flash drum bottoms stream 64 is sent to the second side 70 of the split shell stabilizer 66 to provide a first overhead stream 72 and second over head stream 74, subsequently combined to provide a common overhead stream 76 that includes hydrocarbons having less than or equal to 4 carbon atoms. A first isomerized stabilized stream 78 including branched hydrocarbons such as iso-hexanes and a second isomerized stabilized stream 80 including branched hydrocarbons such as iso-heptanes are withdrawn from the bottom of the first side 68 and the second side 70 respectively.

It is to be appreciated that the common overhead stream 76 may also include hydrogen, although minor amounts of hydrogen are generally present when the chlorided alumina catalyst is employed. Further, in embodiments where chlorided alumina isomerization catalysts are employed, the common overhead stream 76 further includes chlorides. Referring to the FIGURE, the first isomerized stabilized stream 78 and the second isomerized stabilized stream 80 are subsequently sent to a split shell column 82. The split shell column 82 includes a deisohexanizer 84 and a deisoheptanizer 86 on opposite sides of the wall in the split shell column 82. As illustrated, the first isomerized stabilized stream 78 is passed to the deisohexanizer 84 and the second isomerized stabilized stream 80 is passed to the deisoheptanizer 86. A deisohexanizer recycle stream 88 comprising linear hexane, cyclic hydrocarbons, and monomethyl-branched pentane and a first isomerate product 90 are withdrawn from the deisohexanier 84 and a deisoheptanizer recycle stream 92 comprising linear heptanes and cyclic hydrocarbons and a second isomerate product 94 is withdrawn from the deisoheptanizer 86. The deisohexanizer recycle stream 88 is recycled to the inlet of the first isomerization unit 40 as shown in the FIGURE by stream A being mixed with the net first flash drum bottoms stream 38. The deisoheptanizer recycle stream 92 is recycled to the inlet of second isomerization unit 54 as shown in the FIGURE by stream B being mixed with the second separated stream 24. The first isomerate product 90 and the second isomerate product 94 are combined to provide a net isomerate product 96. Further, a common overhead stream 98 comprising light isomerate product is also withdrawn from top of the split shell column 82.

Also, in some embodiments, the second isomerization unit 54 may not include a corresponding deisoheptanizer. Alternatively, the second isomerization unit 54 may only include a dehexanizer, and there may be no recycle to the second isomerization unit 54.

Specific Embodiments

While the following is described in conjunction with specific embodiments, it will be understood that this description is intended to illustrate and not limit the scope of the preceding description and the appended claims.

A first embodiment of the invention is a process for isomerizing hydrocarbons, wherein the process comprises providing a first hydrocarbon feed comprising hydrocarbons having from 5 to 7 carbon atoms; fractionating the first hydrocarbon feed to produce a first separated stream comprising hydrocarbons having from 5 to 6 carbon atoms and comprising benzene and a second separated stream comprising hydrocarbons having 7 carbon atoms; contacting the first separated stream with a benzene saturation catalyst at benzene saturation conditions to produce an intermediate stream comprising cyclohexane; isomerizing the intermediate stream in the presence of a first isomerization catalyst and hydrogen under first isomerization conditions to produce a first isomerized stream; and isomerizing the second separated stream in the presence of a second isomerization catalyst and hydrogen under second isomerization conditions to produce a second isomerized stream. An embodiment of the invention is one, any or all of prior embodiments in this paragraph up through the first embodiment in this paragraph, wherein first isomerization conditions comprise a temperature of about 130° C. to about 210° C. An embodiment of the invention is one, any or all of prior embodiments in this paragraph up through the first embodiment in this paragraph, wherein the second isomerization conditions comprise a temperature of about 100° C. to about 120° C. An embodiment of the invention is one, any or all of prior embodiments in this paragraph up through the first embodiment in this paragraph, wherein the benzene saturation conditions comprise a temperature of about 130° C. to about 160° C. and a pressure of about 18 Kg/cm$^2$ g to about 22 Kg/cm$^2$ g. An embodiment of the invention is one, any or all of prior embodiments in this paragraph up through the first embodiment in this paragraph further comprising passing the intermediate stream to a first flash drum, prior to isomerization of the intermediate stream, to separate a first flash drum overhead stream comprising butane and lighter boiling hydrocarbons and gases. An embodiment of the invention is one, any or all of prior embodiments in this paragraph up through the first embodiment in this paragraph further comprising stabilizing the first isomerized stream and the second isomerized stream to provide a common overhead stream comprising hydrocarbons having less than or equal to 4 carbon atoms and a first isomerized stabilized stream comprising branched hydrocarbons and a second isomerized stabilized stream comprising branched hydrocarbons. An embodiment of the invention is one, any or all of prior embodiments in this paragraph up through the first embodiment in this paragraph, wherein the first isomerized stream and the second isomerized stream are stabilized in a split shell stabilizer, wherein a first side of the split shell stabilizer is configured to stabilize the first isomerized stream and a second side of split shell stabilizer is configured to stabilize the second isomerized stream. An embodiment of the invention is one, any or all of prior embodiments in this paragraph up through the first embodiment in this paragraph further comprising providing the first isomerized stabilized stream to a deisohexanizer to provide a deisohexanier recycle stream comprising linear hexane, cyclic hydrocarbons, and monomethyl-branched pentane and a first isomerate product, wherein the deisohexanier recycle stream combines with the first separated stream. An embodiment of the invention is one, any or all of prior embodiments in this paragraph up through the first embodiment in this paragraph further comprising providing the second isomerized stabilized stream to a deisoheptanizer to provide a deisoheptanizer recycle stream comprising linear heptanes and cyclic hydrocarbons and a second isomerate product, wherein the deisoheptanizer recycle stream combines with the second separated stream. An embodiment of the invention is one, any or all of prior embodiments in this paragraph up through the first embodiment in this paragraph, wherein the first isomerized stabilized stream and the second isomerized stabilized stream are provided to a split shell column comprising the deisohexanizer and the deisoheptanizer. An embodiment of the invention is one, any or all of prior embodiments in this paragraph up through the first embodiment in this paragraph further comprising passing the second isomerized stream through a second flash drum prior to stabilizing the second isomerized stream. An embodiment of the invention is one, any or all of prior embodiments in this paragraph up through the first embodiment in this paragraph, wherein the first isomerization catalyst is one of a zirconia containing catalyst or a chlorided alumina catalyst. An embodiment of the invention is one, any or all of prior embodiments in this paragraph up through the first embodiment in this paragraph, wherein the second isomerization catalyst is one of a zirconia containing catalyst or a chlorided alumina catalyst.

A second embodiment of the invention is a process for isomerizing hydrocarbons, wherein the process comprises providing a first hydrocarbon feed comprising hydrocarbons having from 5 to 7 carbon atoms; fractionating the first hydrocarbon feed to produce a first separated stream comprising hydrocarbons having from 5 to 6 carbon atoms and comprising benzene and a second separated stream comprising hydrocarbons having 7 carbon atoms; contacting the first separated stream with a benzene saturation catalyst at benzene saturation conditions to produce an intermediate stream comprising cyclohexane; separating a first flash drum overhead stream comprising butane and lighter boiling hydrocarbons and gases from the intermediate stream in a first flash drum to provide a net first flash drum bottoms stream; isomerizing the net first flash drum bottoms stream in the presence of a first isomerization catalyst and hydrogen under first isomerization conditions to produce a first isomerized stream; and isomerizing the second separated stream in the presence of a second isomerization catalyst and hydrogen under second isomerization conditions to produce a second isomerized stream; separating a second flash drum overhead stream comprising butane and lighter boiling hydrocarbons and gases from the second isomerized stream in a second flash drum to provide a second flash drum bottoms stream; stabilizing the first isomerized stream and second flash drum bottoms stream to provide a first isomerized stabilized stream and a second isomerized stabilized stream; and passing the first isomerized stabilized stream and the second isomerized stabilized stream to a split shell column comprising a deisohexanizer and a deisoheptanizer to provide a net isomerate product.

A third embodiment of the invention is an apparatus for isomerizing hydrocarbons, wherein the apparatus comprises a first fractionation unit adapted to fractionate a first hydrocarbon feed comprising hydrocarbons having from 5 to 7 carbon atoms to produce a first separated stream comprising hydrocarbons having from 5 to 6 carbon atoms and a second separated stream comprising hydrocarbons having 7 carbon atoms; a benzene saturation reactor in fluid communication with the first fractionation unit to produce an intermediate stream comprising cyclohexane; a first isomerization unit in fluid communication with the benzene saturation reactor and adapted to receive and isomerize the intermediate stream in the presence of a first isomerization catalyst and hydrogen under first isomerization conditions to produce a first isomerized stream; and a second isomerization unit in fluid communication with the first fractionation unit and adapted to receive and isomerize the second separated stream in the presence of a second isomerization catalyst and hydrogen under second isomerization conditions to produce a second isomerized stream. An embodiment of the invention is one, any or all of prior embodiments in this paragraph up through the third embodiment in this paragraph further comprising a first flash drum in fluid communication with the benzene saturation reactor. An embodiment of the invention is one, any or all of prior embodiments in this paragraph up through the third embodiment in this paragraph further comprising a split shell stabilizer comprising a first side and a second side, wherein a first side of the split shell stabilizer is in fluid communication with the first isomerization unit and a second side of split shell stabilizer is in fluid communication with the second isomerization unit. An embodiment of the invention is one, any or all of prior embodiments in this paragraph up through the third embodiment in this paragraph further comprising a split shell column comprising a deisohexanizer and a deisoheptanizer, wherein the deisohexanizer is in fluid communication with the first side of the split shell stabilizer and the deisoheptanizer is in fluid communication with the second side of the split shell stabilizer. An embodiment of the invention is one, any or all of prior embodiments in this paragraph up through the third embodiment in this paragraph further comprising a second flash drum, wherein the second flash drum is in fluid communication with the second isomerization unit. An embodiment of the invention is one, any or all of prior embodiments in this paragraph up through the third embodiment in this paragraph, where in the second flash drum is stacked with the first flash drum.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A process for isomerizing hydrocarbons, wherein the process comprises:
   providing a first hydrocarbon feed comprising hydrocarbons having from 5 to 7 carbon atoms;
   fractionating the first hydrocarbon feed to produce a first separated stream comprising hydrocarbons having from 5 to 6 carbon atoms and less than about 5 wt-% hydrocarbons having more than 6 carbon atoms and comprising benzene and a second separated stream comprising hydrocarbons having 7 carbon atoms;
   contacting the first separated stream with a benzene saturation catalyst at benzene saturation conditions to produce an intermediate stream comprising cyclohexane;
   passing the intermediate stream to a first flash drum, prior to isomerization of the intermediate stream, to separate a first flash drum overhead stream comprising butane and lighter boiling hydrocarbons and gases;
   isomerizing the intermediate stream in the presence of a first isomerization catalyst and hydrogen under first isomerization conditions to produce a first isomerized stream; and
   isomerizing the second separated stream in the presence of a second isomerization catalyst and hydrogen under second isomerization conditions to produce a second isomerized stream.

2. The process of claim 1, wherein first isomerization conditions comprise a temperature of about 130° C. to about 210° C.

3. The process of claim 1, wherein the second isomerization conditions comprise a temperature of about 100° C. to about 120° C.

4. The process of claim 1, wherein the benzene saturation conditions comprise a temperature of about 130° C. to about 160° C. and a pressure of about 18 $Kg/cm^2$ g to about 22 $Kg/cm^2$ g.

5. The process of claim 1 further comprising stabilizing the first isomerized stream and the second isomerized stream to provide a common overhead stream comprising hydrocarbons having less than or equal to 4 carbon atoms and a first isomerized stabilized stream comprising branched hydrocarbons and a second isomerized stabilized stream comprising branched hydrocarbons.

6. The process of claim 5, wherein the first isomerized stream and the second isomerized stream are stabilized in a split shell stabilizer, wherein a first side of the split shell stabilizer is configured to stabilize the first isomerized stream and a second side of split shell stabilizer is configured to stabilize the second isomerized stream.

7. The process of claim 5 further comprising providing the first isomerized stabilized stream to a deisohexanizer to provide a deisohexanier recycle stream comprising linear hexane, cyclic hydrocarbons, and monomethyl-branched pentane and a first isomerate product, wherein the deisohexanier recycle stream combines with the first separated stream.

8. The process of claim 7 further comprising providing the second isomerized stabilized stream to a deisoheptanizer to provide a deisoheptanizer recycle stream comprising linear heptanes and cyclic hydrocarbons and a second isomerate product, wherein the deisoheptanizer recycle stream combines with the second separated stream.

9. The process of claim 8, wherein the first isomerized stabilized stream and the second isomerized stabilized stream are provided to a split shell column comprising the deisohexanizer and the deisoheptanizer.

10. The process of claim 5 further comprising passing the second isomerized stream through a second flash drum prior to stablizing the second isomerized stream.

11. The process of claim 1, wherein the first isomerization catalyst is one of a zirconia containing catalyst or a chlorided alumina catalyst.

12. The process of claim 1, wherein the second isomerization catalyst is one of a zirconia containing catalyst or a chlorided alumina catalyst.

13. A process for isomerizing hydrocarbons, wherein the process comprises:
   providing a first hydrocarbon feed comprising hydrocarbons having from 5 to 7 carbon atoms;
   fractionating the first hydrocarbon feed to produce a first separated stream comprising hydrocarbons having from 5 to 6 carbon atoms and less than about 5 wt-% hydrocarbons having more than 6 carbon atoms and comprising benzene and a second separated stream comprising hydrocarbons having 7 carbon atoms;
   contacting the first separated stream with a benzene saturation catalyst at benzene saturation conditions to produce an intermediate stream comprising cyclohexane;
   separating a first flash drum overhead stream comprising butane and lighter boiling hydrocarbons and gases from the intermediate stream in a first flash drum to provide a net first flash drum bottoms stream;

isomerizing the net first flash drum bottoms stream in the presence of a first isomerization catalyst and hydrogen under first isomerization conditions to produce a first isomerized stream;

isomerizing the second separated stream in the presence of a second isomerization catalyst and hydrogen under second isomerization conditions to produce a second isomerized stream;

separating a second flash drum overhead stream comprising butane and lighter boiling hydrocarbons and gases from the second isomerized stream in a second flash drum to provide a second flash drum bottoms stream;

stabilizing the first isomerized stream and second flash drum bottoms stream to provide a first isomerized stabilized stream and a second isomerized stabilized stream; and passing the first isomerized stabilized stream and the second isomerized stabilized stream to a split shell column comprising a deisohexanizer and a deisoheptanizer to provide a net isomerate product.

* * * * *